United States Patent
Naser et al.

[11] Patent Number: 5,821,065
[45] Date of Patent: Oct. 13, 1998

[54] IMMUNOASSAY FOR THE DETECTION OF COLLAGEN I

[75] Inventors: Werner Naser, Weilheim; Brigitte Dräger, Tutzing; Ulrich Essig, Planegg; Christa Hübner-Parajsz, Tutzing; Erasmus Huber, Finning, all of Germany

[73] Assignee: Boehringer Mannheim GmbH, Mannheim, Germany

[21] Appl. No.: 576,039

[22] Filed: Dec. 21, 1995

[30] Foreign Application Priority Data

Dec. 23, 1994 [DE] Germany .......................... 44 46 232.8
Feb. 1, 1995 [DE] Germany ........................ 195 03 146.6

[51] Int. Cl.$^6$ ..................................................... G01N 33/53
[52] U.S. Cl. ........................... 435/7.1; 435/7.2; 435/7.93; 435/810
[58] Field of Search ............................. 435/7.1, 810, 7.2, 435/7.93

[56] References Cited

FOREIGN PATENT DOCUMENTS

WO 92/21698  12/1992  WIPO .

OTHER PUBLICATIONS

Burgess et al (J. Cell Bio, 111: 2129–2138, (1990).
Tao et al, 1989, (J. Immunol, 143: 2595–2601, 1989).
Lazar et al, (Mol & Cel Bio, 1988, 8: 1247–1252).
Herbert et al, Dictionary of Immunology, 4th Ed, Academic Press, London, pp. 3 & 147, 1995.
Bonde et al. Clin Chem. 40 (11) 2022, 2025, Nov. 1994.
Harlow & Lane Cold Spr Harbor Laboratory Press Ch. 14, 1988.

*Primary Examiner*—Lila Feisee
*Assistant Examiner*—Susan Ungar
*Attorney, Agent, or Firm*—Nikaido Marmelstein Murray & Oram LLP

[57] ABSTRACT

A method for determining collagen degradation products in a body fluid sample using a non-competitive or competitive immunoassay is disclosed, the method comprising incubating the body fluid sample with an amount of antibody which specifically reacts with the amino acid sequence of SEQ ID NO. 2 of collagen 1 or a fragment thereof, and determining the collagen degradation products bound to the amount of the antibody. A kit for such a method is also disclosed.

10 Claims, 7 Drawing Sheets

1

IMMUNOASSAY FOR THE DETECTION OF COLLAGEN I

The invention addresses antigens for the preparation of antibodies to N-termini of collagen 1α2 chains, a method for preparing such antigens, antibodies to N-termini of collagen 1α2 chains that were obtained by immunization using the antigen in accordance with the invention; the invention also concerns the use of these antibodies for the detection of collagen.

Collagen is an important structural protein in the connective tissue of skin, cartilage, and bones. There are 11 known types of collagen, each of which consists of three chains referred to as α1, α2, and α3 (E. Miller et al. in Methods in Enzymology 144, Structural and Contractile Proteins, ed. L. Cunningham, Academic Press Inc. 1987, p. 3–41). One characteristic property of mature collagen of certain tissue, particularly bone or cartilage, is the cross-linking of adjacent fibers by hydroxylysylpyridinolin or lysylpyridinol (D. Fujimoto et al., J Biochem 83 (1978), 863–867; D. Eyre et al., Ann. Rev. Biochem. 53 (1984), 717–748 and D. Eyre, Methods in Enzymology 144 (1987), 115–139). These cross-links can be used as a biochemical label for the specific detection of collagen (Z. Gunja-Smith et al., Biochem. J. 197 (1981), 759–762). When extracellular collagen is degraded, hydroxylysylpyridinolin or lysylpyridinolin derivatives which contain peptide side chains or free pyridinolin derivatives with lysyl or hydroxylysyl residues as described in WO 91/10141 are released into body fluids such as blood or urine. The detection of these compounds in body fluids, hence, provides information on the degradation of extracellular collagen, e.g. in case of osteoporosis and as a consequence of tumors of the bone tissue. For the detection of these hydroxylysyl or lysylpyridinolin with peptide side chains, WO89/12824 de scribes monoclonal antibodies that were obtained by immunization using corresponding cross-linked collagen fragments that were isolated from urine. The methods described in WO 91/08478 and WO 92/21698 also describe the detection of collagen via an antibody to naturally, i.e. in vivo, generated cross-linked degradation products of collagen.

A drawback of these natural sources of isolated peptides is that there is no reliable source for reproducibly preparing the antigens or binding partners used in the test. Another disadvantage of these natural sources of isolated peptides is the risk of contamination with infectious material.

Defined antigens can be obtained by chemically synthesizing a peptide which corresponds to an epitope of the antigens. If small peptides with a molecular weight of approximately 700–1500 D are used, it is necessary to have a binding to a carrier molecule to obtain an antigen with an immunogenic effect. The binding of the carrier molecule must not alter the structure of the epitope. To date, the carrier molecule is preferably coupled to the ends of the peptide chain at a sufficiently large distance away from the assumed epitope area (Laboratory Technics in Biochemistry and Molecular Biology, Synthetic Polypeptides as Antigens, Editors R. H. Burdon and P. H. van Knippenberg, Elsevier, Amsterdam, New York, Oxford 1988, pages 95–100).

A problem occurring in the chemical synthesis of a defined antigen which corresponds to a natural degradation product of the cross-linked collagen is the hydroxylysyl or lysyl pyridinoline structure resulting from the cross-linking as the chemical synthesis of this structure is difficult to accomplish.

To date, investigators have assumed that the detection of collagen or collagen degradation products in a sample required the detection of cross-linking structures per se or so-called cross-linked peptides which are a result of the cross-linking of the hydroxylysyl or lysyl residues as these hydroxylysyl or lysylpyridinoline structures are characteristic for collagen. Examples for such detection methods are described in WO 89/12824, WO91/08478, WO89/04491 and WO91/10141.

German patent DE 42 25 038 showed for the first time that it is also possible to use linear, non cross-linked peptide sequences and antibodies for the detection of collagen or collagen fragments. The immunogens used are short peptides which correspond to a linear partial sequence of collagen and contain at least one lysine residue that is present in the natural collagen molecule as hydroxylysine. The peptide is bound to a carrier molecule via the ε-amino group of this lysine residue.

WO 94/03813 also describes synthetic linear peptides which correspond to a sequence of the non-helical C- or N-terminal area of collagen as antigens for the preparation of antibodies to collagen or collagen fragments. Synthetic linear peptides are all those continuous amino acid sequences of the non-helical C- or N-terminal area of collagen. These areas are known from Chu et al., Nature 310, 337–340 (1984), Click et al., Biochemistry 9, 4699–4706 (1970), Morgan et al., J. Biol. Chem. 245, 5042–5048 (1970) and Bernard et al., Biochemistry 22, 5213–5223 (1983). Especially peptides found in the C-terminal area of the α-chain of collagen were disclosed. The antibodies obtained with these immunogens can be used in immunoassays for the detection of collagen degradation products in body fluids.

It was, hence, the object of the present invention to further improve this type of immunoassay and optimize the material such as antibodies and antigens used for this purpose. The antibodies must be distinguished by the fact that they specifically recognize collagen degradation products, i.e. collagen fragments that occur in body fluids.

Subject matter of the present invention is, hence, an antibody to collagen degradation product of collagen 1 in body fluids which specifically recognizes the amino acid sequence Val-Gly-Leu-Gly SEQ ID NO: 2 within collagen l or fragments thereof. This amino acid sequence corresponds to the amino acid residues 7 to 10 at the N-terminal end of type l collagen α2 chain. Experience has surprisingly shown that when this antibody is used in an immunoassay for the detection of collagen degradation products, it is possible to very specifically and sensitively detect the collagen degradation products in these body fluids, and that such an immunoassay shows a very good correlation to an immunoassay where antibodies to cross-linked collagen degradation products are used (WO 89/04491).

The antibodies of the invention specifically recognize the amino acid sequences Val-Gly-Leu-Gly SEQ ID NO: 2, i.e. this amino acid sequence is recognized within the collagen degradation products contained in body fluids. The amino acids that are adjacent to the sequence also can be recognized by the antibodies. This, however, is not a prerequisite to be satisfied by the antibody of the invention, as these amino acids also can be missing in some collagen fragments. It is of critical importance that the antibody recognize the epitope characterized by the sequence Val-Gly-Leu-Gly SEQ ID NO: 2 within a collagen fragment. The epitope bound by the antibody may be longer by some amino acids, e.g. 1–4 amino acids. Particularly preferred antibodies recognize the amino acid sequence 6–13 of the N-terminal end of the type 1 collagen α2 chain.

The antibodies can be obtained in conventionally used methods. For immunization from body fluids, it is, for example, possible to use purified collagen fragments which contain the N-terminal type 1α2 chains including the sequence Val-Gly-Leu-Gly SEQ ID NO: 2. These collagen fragments can also be obtained by enzymatic or chemical cleavage of type 1 collagen. The antibodies formed to these more or less exactly defined peptides must be selected and purified in a suitable screening procedure after immunization. To accomplish this, one uses the reaction of the antibodies to short peptides containing the sequences Val-Gly-Leu-Gly SEQ ID NO: 2.

A considerably more simple and, hence, preferred way of preparing the antibodies is to immunize animals with a synthetic peptide or peptide derivative which contains an amino acid sequence corresponding to SEQ ID NO 1 or a partial sequence thereof, which contains at least the amino acid sequences Val-Gly-Leu-Gly SEQ ID NO: 2. The synthetic peptide preferably contains at least 6 amino acids. The amino acids added in addition to the sequence Val-Gly-Leu-Gly SEQ ID NO: 2 are preferably attached to the N- or C-terminal end of this sequence which are also adjacent to the sequence in the type 1 collagen α2 chain. It is, however, also possible to add other amino acids. As is conventionally done, the peptides are coupled to an immunogenic carrier such as Keyhole Limpet Hemocyanine (KLH), bovine serum albumin, or edestin to increase the immune response. The antibodies in accordance with the invention can be polyclonal or monoclonal antibodies, with monoclonal antibodies being preferred.

Depending on the use in different amino acids for the detection of collagen degradation products, the antibodies can be coupled with a signal-generating substance or a labeling group such as fluorescence-labeling groups, electrochemiluminescence-labeling groups, digoxin, biotin, or radioactive groups. When immunoassays are used which require a solid phase, the antibodies can be coupled to this phase either directly or indirectly. The coupling of these groups or the solid phases is accomplished according to methods that are known to the expert.

Another subject matter of the invention are peptides or peptide derivatives which contain an amino acid sequence corresponding to SEQ ID NO 1 or a partial sequence thereof which contains at least the amino acid sequence Val-Gly-Leu-Gly SEQ ID NO: 2. The amino acid sequences are partial segments from the N-terminal non-helical end of the type 1 collagen α2 chain. The peptides or peptide derivatives can be used as immunogens for the preparation of the antibodies of the invention, as specific binding partners, and as standard materials in immunoassays. The peptides of the invention can be generated by means of known methods of synthesis using chemical procedures or by cloning and expressing a DNA sequence which codes with these peptides in a suitable host cell.

In addition to the peptides, the invention also relates to peptide derivatives. This term includes peptides where one or several amino acids have been derivatized in a chemical reaction. Examples are in particular those molecules where the backbone and/or free amino acid groups have been derivatized. The peptide derivatives in accordance with the invention have an essentially equivalent specificity and/or affinity for binding to the antibody of the invention.

Peptide derivatives are also peptide-mimetic substances which exhibit an essentially equivalent specificity and/or affinity for the binding to the antibodies in accordance with the invention as do the above-mentioned peptides. Peptide-mimetic substances are compounds which can replace peptides in their interaction with the antibodies and have an increased stability as compared to native peptides. Method for the preparation are described in Giannis and Kolter, Angew. Chem. 105 (1993), 1303–1326, Lee et al., Bull. Chem. Soc. Jpn. 66 (1993), 2006–2010 and Dorsch et al., Kontakte (Darmstadt) (1993) (2), 48–56.

Depending on the use as an immunogen for the preparation of the antibodies or as a material used in immunoassays, the peptides or peptide derivatives of the invention can be coupled to immunogenic carriers which are as described above signal generating substances or labeling groups such as fluorescence-labeling groups, digoxin, biotin or radioactive groups. In the case of immunoassays in which a solid phase is required, the peptides or peptide derivatives can be directly or indirectly linked to this solid phase via a streptavidin/biotin link, for example; solid phases include tubes, beads, latex particles and the like. The coupling is accomplished according to conventionally known methods.

As already mentioned, the peptides or peptide derivatives in accordance with the invention can be used for the preparation of antibodies.

Another subject matter of the invention is a method for preparing antibodies to collagen degradation products by means of immunization with a peptide or peptide derivative of the invention which contains the amino acid sequence corresponding to SEQ ID NO 1 or a partial sequence thereof which contains at least the amino acid sequence Val-Gly-Leu-Gly SEQ ID NO: 2. In a preferred manner, the peptide or peptide derivative has a length of at least 6 amino acids and is coupled to an immunogenic carrier. Once immunization is completed, the desired antibodies are isolated from the serum of the immunized animals according to known methods. Isolation of the desired antibody is preferably carried out via immunoadsorption to a peptide coupled to a carrier, preferably sepharose; this peptide contains the amino acid sequence corresponding to SEQ ID NO 1 or a partial sequence thereof, which at least contains the amino acid sequence Val-Gly-Leu-Gly SEQ ID NO: 2.

The preferred subject matter of the invention is a method for preparing monoclonal antibodies to cross-linked collagen by immunization of the peptide or peptide derivative in accordance with the invention, immortalizing the spleen cells of the immunized animals, cloning those immortalized spleen cells which produce the desired antibody, and isolating the antibody from the cloned cells or the culture supernatant of the cells.

Immunization is accomplished with the aid of conventionally available animals, preferably mice or rabbits.

The spleen cells of the immunized animals are immortalized according to methods that are known to the expert, e.g. the hybridoma technology (Köhler and Milstein, Nature 256 (1975), 495–497) or by transformation with the Epstein-Barr virus (EBV transformation). For the detection of those immortalized cells which produce the desired antibodies, a sample of the culture supernatant is incubated in a conventional immunoassay with the peptide of the invention used for the immunization; subsequently a test is carried out to see whether or not an antibody binds to this peptide or peptide derivative.

The concentration of degradation products of collagen is an important diagnostic marker for the extent of an osteolysis. With the aid of polyclonal or monoclonal antibodies of the invention, it is, hence, possible to determine the degree of an osteolysis by determining the concentration of the degradation products of natural collagen in body fluids.

Another subject matter of the invention is, hence, the use of an polyclonal or monoclonal antibody of the invention for the determination of the osteolysis by incubating the antibody with a sample and determining the collagen degradation products bound to the antibodies or by carrying out an immunoassay for the detection of collagen 1 or collagen fragments in a sample using the antibody of the invention.

Samples are body fluids which contain collagen degradation products, preferably serum, plasma, or urine.

Principally, all conventional immunoassays are suitable for the detection. In a preferred manner, the binding of the antibody to collagen 1 or collagen fragments is accomplished with the aid of a competitive test. In a competitive test, the antibody can be incubated with a sample and with the additional peptide or peptide derivative in accordance with the invention both simultaneously or sequentially. The collagen fragments contained in the sample preferably compete with the peptide or the peptide derivative of the invention for the binding to the antibody, so that the binding of the antibody to the hapten in accordance with the invention is a measure for the quantity of antigen contained in the sample. In a heterogeneous competitive immunoassay where the liquid phase is separated from the solid phase, both the antibody or the peptide can be labeled or bound to a solid phase. The exact amount of antigen contained in the sample can then be determined in a conventional manner by comparison with a standard treated in the same manner.

All competitive test formats that are known to the expert can be used for the detection. The detection can be carried out, for example, using the turbidimetric inhibition immunoassay (TINIA) or a latex particle immunoassay (LPIA). When a TINIA is used, the peptide or peptide derivative of the invention is bound to a carrier such as dextrane (EP-A-0 545 350). This polyhapten competes with the analyte contained in the sample for the binding to the antibody. The formed complex can be determined either turbidimetrically or nephelometrically.

When an LPIA is employed, particles, preferably latex particles, are coated with the peptides of the invention and mixed with the antibody of the invention and the sample. When an analyte is present in the sample, agglutination is reduced.

Enzyme immunoassays (Wisdom, G. B., Clin. Chem. 22/8 (1976), 1243–1255 and M. Oellerich, J. Clin. Chem. Clin. Biochem. Vol. 18 (1980), 197–208), fluorescence polarization immunoassays (FPIA) (W. Dandliker et al., J. Exp. Med. 122 (1965), 1029), enzyme-multiplied immunoassay technology (EMIT) (Gunzer et al., Kontake III, 1980, 3–11 and K. Rubenstein, Biochemical and Biophysical Research Communications 47 (1972), 846–851) or the CEDIA technology (Henderson et al., Clinical Chemistry 32 (1986), 1637–41) are also suitable for the detection reaction.

Experience has shown that it is somewhat advantageous to denature the sample or the collagen or collagen fragments contained in the sample to facilitate the binding between epitopes and antibodies. Prior to incubation with the antibody, experience has shown to be most suitable to treat the sample with the denaturing agent for proteins which are known to the expert. To reduce interference during the immunological reaction between the sample and the specific antibodies to the lowest possible degree or entirely, the denatured probe is again diluted prior to incubation with the antibody. Possible denaturing agents are all agents known to the expert. Potassium rhodanide (KSCN) at a concentration between 2 and 6M and tetradecyltriethylammonium bromide (TTAB) at a concentration between 0.5 and 2M have proven to be particularly suitable for denaturing.

Another subject matter of the invention is a standard material to prepare a standard or calibration curve in an immunoassay for the detection of collagen 1 or collagen fragments, characterized in that it contains a peptide or a peptide derivative which contains the amino acid sequence of SEQ ID NO 1 or a partial sequence thereof which in turn contains at least the amino acid sequence Val-Gly-Leu-GlySEQ ID NO: 2.

Figure 1:
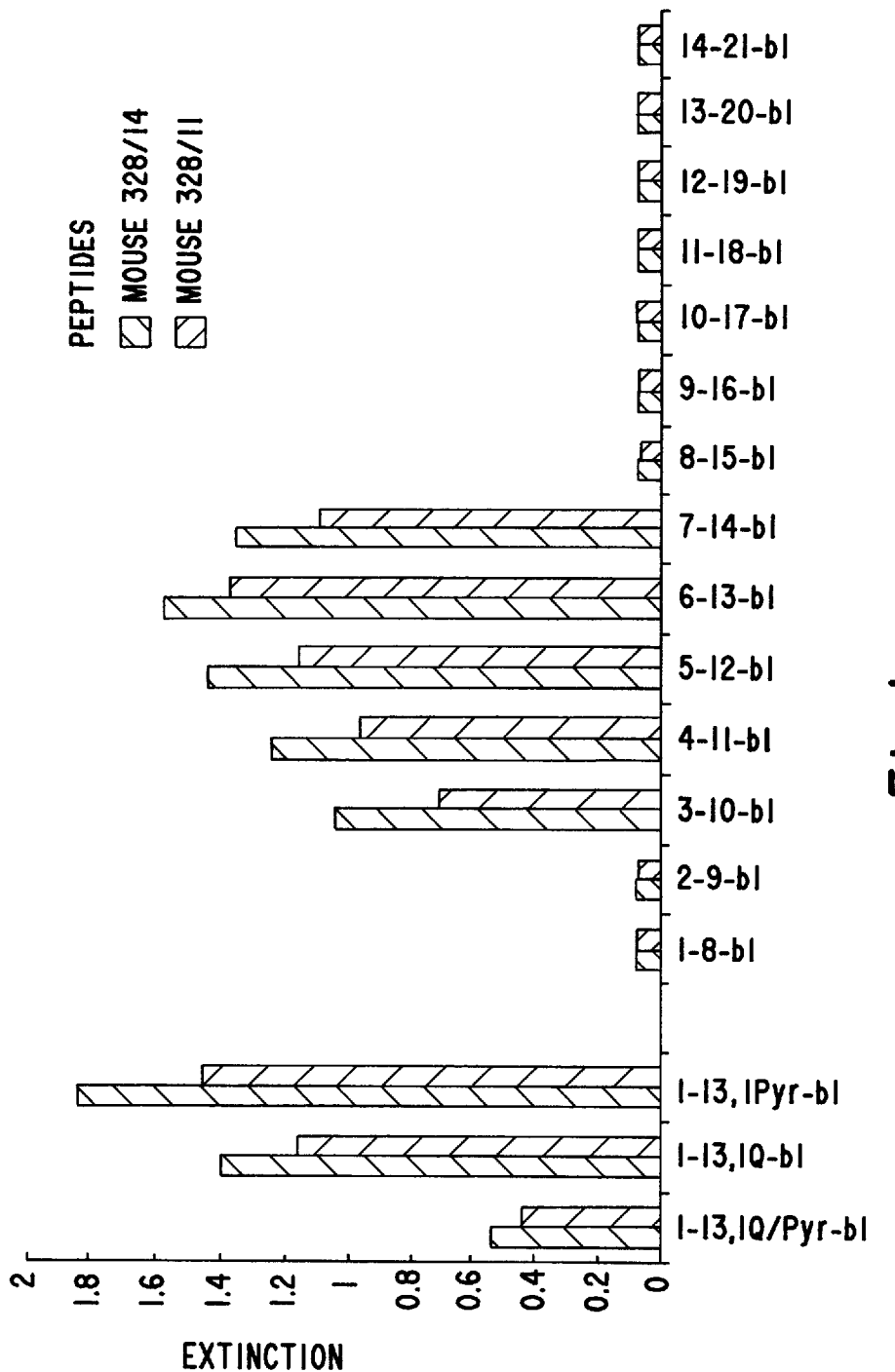
FIG. 1 shows a PEPSCAN® measurement of mouse serum binding to various sequences of collagen 1.

The invention is hereinafter illustrated in greater detail in connection with the sequence protocol.

SEQ ID NO 1 shows the sequence of a peptide in accordance with the invention which corresponds to the amino acids 1–13 of the N-terminal end of type 1 collagen α2 chain. Xaa means Gln or Pyr (pyroglutamine).

EXAMPLE 1

1.1 Peptide synthesis

Peptide 1 which contain a partial sequence of the amino acid sequence of collagen corresponding to SEQ ID NO 1 (1 Gln-Tyr-Asp-Gly-Lys-Gly-Val-Gly-Leu-Gly-Pro-Gly-13Pro)-Cys SEQ ID NO: 1(=CollIα(1–13, 1 Gln)-Cys) and peptide 2 (1 Pyr-Tyr-Asp-Gly-Lys-Gly-Val-Gly-Leu-Gly-Pro-Gly-13Pro)-Cys SEQ ID NO: 1(=CollIα2(1–13, 1 Pyr)-Cys) are obtained via fluorenylmethyloxy-carbonyl-(Fmoc)-solid phase peptide synthesis using a Labortec SP 640 peptide synthesizer. The following 4.0 equivalents of the following Fmoc amino acid derivatives are used:

Tyr with tert. butyl protective group

Lys with tert. butyloxycarbonyl protective group

Cys with S-tert. butyl protective group.

All remaining amino acid derivatives (Gln, Pyr, Asp, Gly, Val, Leu, Pro) were used without a side chain protection group.

The amino acids or amino acid derivatives are dissolved in N-methylpyrrolidone. The peptide is synthesized on 3 g of 4-(2',4'-dimethoxy-phenyl-Fmoc-amino methyl) phenoxy resin (Tetrahedron Letters 28 (1987), 2107) with a concentration of 0.87 mmol/g of resin (JACS 95 (1973), 1328). The coupling reactions for the Fmoc amino acid derivative are carried out for 60 minutes with 4,4 equivalents of dicyclohexylcarbodiimide and 4,8 equivalents of N-hydroxybenzotriazol in dimethylformamide as a reaction medium. The success of the coupling reaction is monitored with the aid of the Kaiser test (Anal. Biochem. 34 (1970), 595) on synthetic resin washed with isopropanol. The coupling is repeated under the above-listed conditions until a complete conversion has been achieved. After each synthesis step, the Fmoc group is cleaved off using 20% piperidine in dimethylformamide over a period of 20 minutes. The concentration in the resin is determined via UV absorption of the released fulven group after each piperidin treatment.

After the synthesis, the concentration is still at 0.68 mmol/g. Release of the peptide from the synthesis resin and the cleaving of the acid-labile protective groups is accomplished with 80 ml trifluoroacetic acid, 5 ml ethanedithiol, 2.5 g phenol, 2.5 ml m-Cresol, and 5 ml of water in 60 minutes at room temperature. The reaction solution is then concentrated in a vacuum and the residue is taken up in diisopropylether, stirred vigorously for 0.5–2 hours and then filtered. The material is then subject to prepurification via gel permeation chromatography using Sephadex G15, with 0.5% acetic acid as an eluting agent. The resulting raw material is then filtered and isolated in 120 minutes with a preparative HPLC on Nucleosil RP18 (column 40 mm×250 mm 300 Å, 5 $\mu$m) using a gradient of 100% reagent A (water, 0.1%, trifluoroacetic acid) to 100% reagent B (60% acetonitrile, 40% water, 0.1% trifluoroacetic acid). The identity of the eluted material is checked via ionic spray mass spectrometry.

1.2 Immunogen synthesis

Activation of KLH using maleinimido-propionic acid-N-succinimide ester (=MPS)

280 mg of KLH lyophilisate are dissolved in 15 ml of 0.1M potassium phosphate buffer pH 7.0; then a solution of 7.35 mg MPS=maleinimido-propionic acid-N-hydroxysuccinimide ester in 1 ml DMSO is added and stirred for 16 h at room temperature. Subsequently, the mixture is centrifuged and the supernatant is purified via an AcA 202 column (d=5 cm; l=25 cm; equilibrated with 0.1M potassium phosphate buffer pH 7.0).

Yield: 129 mg of KLH-MP (4.3×10Hu −5 mmol); $\eta$=3.59 mg/ml (determined with a BCA Test; BCA Protein Assay Reagent, Pierce).

Reaction of KLH-MP with Coll1$\alpha$2(1–13, 1Gln/Pyr)-Cys

A mixture of 20.33 mg of Coll$\alpha$2(1–13, 1 Gln)-Cys and 20.08 mg of Coll1$\alpha$2(1–13, 1 Pyr)-Cys are dissolved in 1 ml $H_2O$ and for solution added to the MP-activated KLH. The mixture is stirred for 16 hours at room temperature. Subsequently, the mixture is centrifuged and the supernatant is purified via an AcA 202 column (d=5 cm; l=25 cm; equilibrated with 0.1M potassium phosphate buffer pH 7.0).

Activation of BSA with MPS 150 mg of BSA are dissolved in 10 ml of 0.1M potassium phosphate buffer pH 7.0, a solution of 11.6 mg MPS in 1 ml DMSO is added and the mixture stirred for 16 h at room temperature. Subsequently, the solution is purified by an AcA 202 column (d=5 cm; l=25 cm; equilibrated with 0.1M potassium phosphate buffer pH 7.0).

Yield: 121 mg BSA-MP ($1.75\times10^3$ mmol/l); $\eta$=3.78 mg/ml (determined with a BCA test).

Reaction of BSA-MP with Coll1$\alpha$2(1–13, 1 Gln/Pyr)-Cys

A mixture of 47.13 mg of Coll1$\alpha$2(1–13, 1 Gln)-Cys and 46.53 mg of Coll1$\alpha$2(1–13, 1 Pyr)-Cys is dissolved in 3 ml of $H_2O$ and for solution added to MP-activated BSA. The solution is stirred for 16 h at room temperature. Subsequently, the solution is purified by an AcA 202 column (d=5 cm; l=25 cm; equilibrated with 0.1M potassium phosphate buffer pH 7.0).

Yield: 124 mg immunogen; $\eta$=2.59 mg/ml (determined with a BCA test).

1.3 Synthesis of the peptides for the PEPSCAN analysis

The peptides were obtained using Fmoc (fluorenyloxycarbonyl) solid phase synthesis. The reactions were carried out in a multiple synthesizer manufactured by Zinsser (SMP 360). The coupling reactions for the Fmoc-amino acid derivative were carried out with 1.1 equivalent of dicyclohexylcarbodiimide and 1.0 equivalent of N-hydroxybenzotriazol over a period of 90 minutes. The reaction medium used was dimethylformamide. The Fmoc group was cleaved using 50% piperidine in DMF over periods of 10 and 20 minutes. 10.0 equivalents of the following Fmoc amino acid derivatives were used: Asp (with tert. butyl-ester protective group: Asp (with tert. butyl-ester protective group), Gly, Lys (with tert. butyloxycarbonyl protective group), Met, Tyr (with tert. butyl protective group).Gln, Val, Leu, Pro, Arg (with PMC protective group).

The peptide was synthesized using 20 mg of Rink resin (polystyrene/1% divinylbenzol) with a load of 0.50 mmol/g.

The procedure generated peptides each containing 8 amino acid residues from the sequence Coll1$\alpha$2(1–21). Gln, Tyr, Asp, Gly, Lys, Gly, Val, Gly, Leu, Gly, Pro, Met, Gly, Leu, Met, Gly, Pro, Arg, Gly SEQ ID NO: 1.

The peptide was released using 1 ml of trifluoroacetic acid, 50 $\mu$l ethanedithiol, 50 $\mu$l of thiocresol, 25 $\mu$l of thioanisol and 25 $\mu$l of water over a period of 3 h at room temperature. The peptide was precipitated from the cleavage solution with dusopropyl ether.

In order to biotinylate the peptide antigen, a highly concentrated mol equivalent (solubility depends on the amino acid sequence) was dissolved in argon-saturated potassium phosphate buffer (0.1 mol/l, pH 8.0) and added to 3 equivalents of D-biotiny-$\epsilon$-amino-aprnic acid-N-hydroxysuccinimide ester dissolved in argon-saturated dimethyl formamide (solution of 1 $\mu$mol reagent in 5 $\mu$l DMF). The reaction mixture is then stirred 2 h at room temperature in an argon atmosphere. The biotinylated product was obtained by separating the low-molecular components via gel filtration over NAP-15 column (pharmacia) followed by lyophilization. The yields range between 40 and 90%. The analysis was carried out via HPLC, HPCE and TLC to obtain the purity, LSI-MS (mole peak) for identity and TLC with specific dyeing reagents (p-dimethylaminocinnemonaldehyde on biotin) and the content was determined by microanalysis.

EXAMPLE 2

Preparation of monoclonal antibodies

Immunization of mice 12 weeks old Balb/c mice were intraperitoneally immunized for the first time with 100 $\mu$g immunogen (Coll1$\alpha$2 (1–13), (1–13, Gln/Pyr)-Cys-KLH or Coll$\alpha$2 (1–13, Gln/Pyr)-Cys-BSA in complete Freund's adjuvans.

After 6 weeks, three additional immunization steps were carried out intraperitoneally in monthly intervals. Each mouse was administered 100 $\mu$g of the immunogen in incomplete Freund's adjuvans.

Eight days after the 4th immunization, blood was taken retro-orbitally to obtain mouse serum for an analysis. The results of the immunization with the peptide which was coupled to KLH (Coll1$\alpha$2 (1–13, Gln/Pyr)-Cys-KLH) were improved as compared to the BSA carrier protein. For additional tests, two mouse sera, 328/14 and 328/11 were selected from the 15 available sera that were immunized with KLH immunogen and characterized in greater detail (see example 3.1).

Additional intravenously administered immunizations with 100 $\mu$g of immunogen in PBS buffer were carried out 3 days, 2 days, and on the last day prior to the fusion.

Fusion and cloning

Preparation of the spleen cell suspension

Mice were killed by breaking their necks and their spleens were removed in a sterile environment. The spleen cells were pressed out of the connective tissue with the aid of a pair of tweezers in RPMI 1640 base medium. The cell suspension was pressed through a steel sieve and subsequently centrifuged in a tube at 200 g in RPMI 1640 base medium.

Fusion

The spleen cells of an immunized mouse were mixed with P3x63Ag8-653 myeloma cells (ATTCC-CRL 8375) in a ratio of 1:5 and centrifuged (10 minutes, 300 g, 4° C.). The cells were again washed with RPMI 1640 base medium and centrifuged at 400 g in a 50 ml tip tube. The supernatant was decanted, the cell sediment was loosened and 1 ml PEG (MG 4000, Merck) was added and passed through a pipette. After 1 minute in a water-bath 5 ml of RPMI 1640 base medium were added drop-wise at room temperature and over a period of 5–6 minutes; the solution was mixed and filled up to 50 ml with medium (RPMI 1640+10% FKS) and subsequently centrifuged for 10 minutes at 400 g, 4° C. The sedimented cells were taken up in the RPMI 1640 medium+ 10% FCS and placed into 24-well cell culture plates with $5 \times 10^4$ spleen cells per well in 1 ml selection medium (100 mM hypoxanthin, 1 µg/ml azaserin in RPMI 1640+10% FCS) (FCS=fetal calf serum).

After 10 days, these primary cultures were tested for specific antibody synthesis (cf. example 3.3). Primary cultures of the corresponding specificity were cloned via FACS (cell sorter) in 96-well cell culture plates. Interleukin-6 (Boehringer Mannheim, Cat. No. 1271172, 100 U/ml) was added to the medium as a growth additive. Six hybridoma cell lines were thus isolated.

EXAMPLE 3

3.1 Pepscan measurement in mouse sera

Microtiter plates (manufactured by Nunc) were coated with thermo-BSA streptavidin and loaded with a solution of 100 ng of the respective biotinylated peptides per ml PBS, 0.05% Tween 20 (100 µl/well). The following peptides were used:

Collla2(1–13, 1 Gln), Collla2(1–13, 1 Pyr), a 1:1 mixture of these two peptides Collla2(1–13, 1Gln, Pyr), Collla2 (1–8), Collla2(2–9) . . . through Collla2(14–21).

After incubation for 1 h at room temperature, the mixture was washed twice with PBS, 0.05% Tween 20. The mice sera 328/14 and 328/11 were diluted 1:4000 in PBS, 0.05% Tween 20; subsequently, 100 µl of this solution was pipetted into the peptide-coated wells and incubated for 1 h at room temperature. Subsequently, the solution was washed 3 times with PBS, 0.05% Tween 20. To carry out the detection of a peptide bound antibody of the respective mouse serum, 100 µl of the POD-labeled Fab fragments of polyclonal sheep antibody to mouse Fc-γ (Boehringer Mannheim, Cat. No. 104 75 23) were added at a concentration of 40 mU POD/ml PBS, 0.05% Tween. After incubation for 1 h at room temperature, the solution was washed 3 times with PBS, 0.05% Tween 20. After adding 100 µl/well of the chromogenic reagent (ABTS®, Boehringer Mannheim, Cat. No. 120 45 21 and 120 45 30) and after 30 minutes of incubation at room temperature, the absorbance was measured at 450/490 nm in a microtiter plate reader manufactured by SLT. The results of the Pepscan measurement is given in FIG. 1. It can be clearly seen that the mouse serum bind to the complete peptides corresponding to SEQ ID NO 1. The Pepscan analysis with the octapeptides with sequences from the N-terminal area of the collagen 1 α2 chains shows that all antibodies recognize the sequence 7–10, i.e. Val-Gly-Leu-Gly SEQ ID NO: 2. This sequence is the main component of the epitope responsible forthe binding of the antibody.

3.2 EIA com petition test

With the antibodies of the mouse sera and a wall-fixed peptide, it is possible to design an enzyme immunoassay according to the competition principle in order to measure collagen peptides in urine; the test shows good correlation to the OSTEMARK® test by Ostex.

Figure 2:
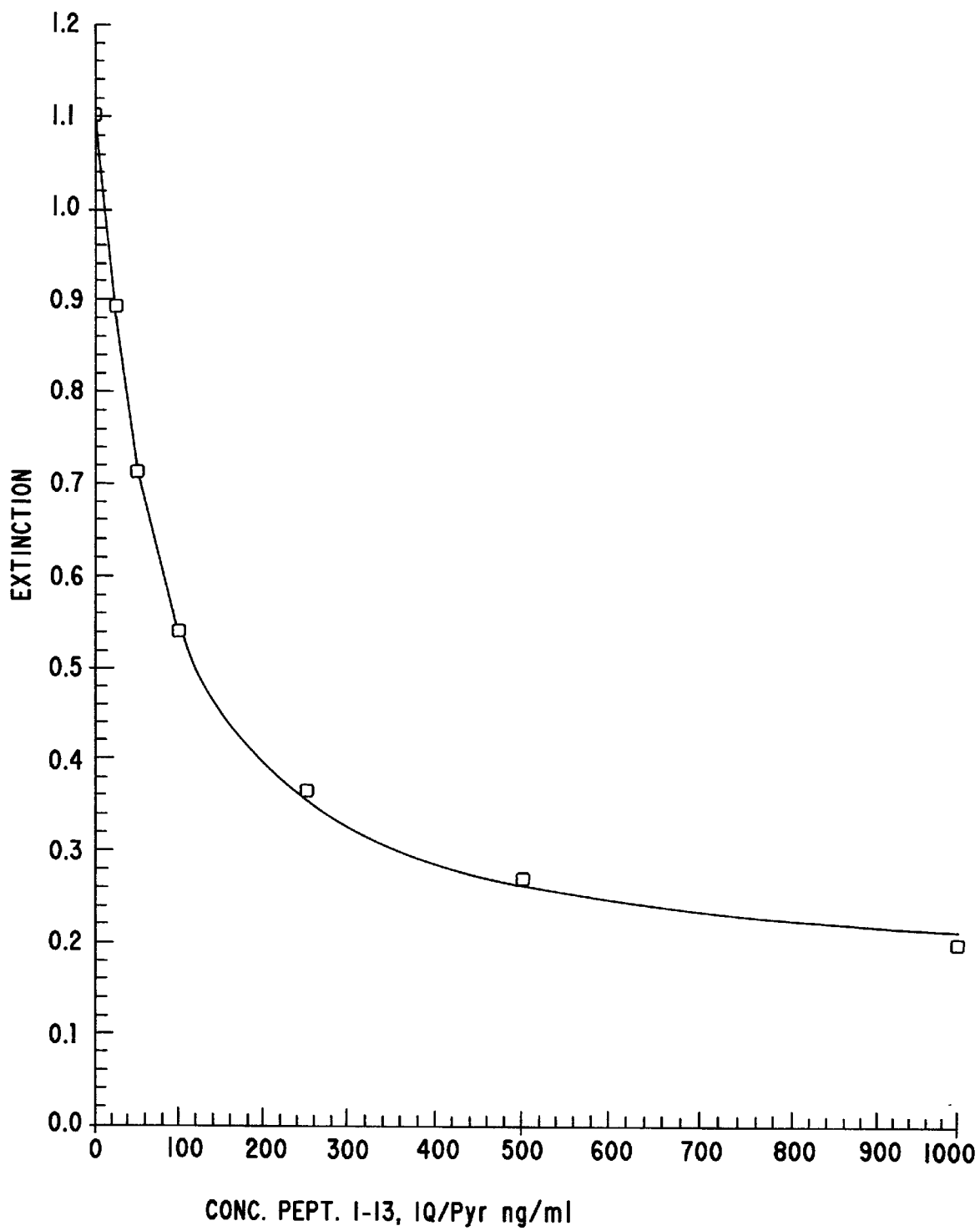
FIG. 2 shows a standard curve obtained with serum taken from mouse328/11. Signal was generated with POD-labeled Fab fragments of a polyclonal antibody to mouse Fcy and plotted against the standard concentration.

Thermo-BSA streptavidin-coated microtiter plates were coated with the biotinylated peptide mixture Collla2(1–13, 1 Gln/Pyr, mixture of 1:1) (100 ng/ml PBS, 0.05% Tween 20, portions of 100 µl/well). After incubation for 1 h at room temperature, the solution was washed twice with PBS, 0.05% Tween 20. Dilutions with PBS, 0.05% Tween 20 were obtained from the peptide mixture Collla2(1–13, Gln/Pyr) in following concentrations: 0, 25, 50, 100, 250, 500 and 1000 ng/ml. 50 µl of the respective standard and 50 µl of the diluted mouse sera were pipetted into each well (mouse serum 328/11, 1:4000 diluted in PBS, 0.05% Tween 20) and mixed. After incubation for 1 h at room temperature, the solution was washed 3 times with PBS, 0.05% Tween 20 and subsequently, as described in the Pepscan measurement example, a measuring signal was generated with the POD-labeled Fab fragment of a polyclonal antibody to mouse Fcγ followed by color reaction. The standard curve is obtained when the measuring signal is plotted against the standard concentration (FIG. 2).

Measurement of the samples (urine)

50 µl of urine were used in the test instead of the standard dilutions. The test was otherwise carried out as was the standard curve. The concentration of the sample was read off the calibration curve and subsequently referred to the creatinine value of the sample. The creatinine value was determined using the Creatini-PAP test manufactured by Boehringer Mannheim (Cat. No.1 178 652), an enzymatic method of determination.

A comparison measurement was carried out with the OSTEOMARK® (an assay for the measurement of cross linked N-telopeptides of type 1 collagen in humine urine) test manufactured by Ostex; the abbreviation BCE means bone collagen equivalents. The results are summarized in the following Table 1:

TABLE 1

| | | Test of the invention | | OSTEOMARK |
|---|---|---|---|---|
| Samples | Absorbance | Concentration ① | Concentration ② | Concentration ③ |
| Osteo-porosis | 0.932 | 16.5 | 14.42 | 432 |
| Paget's disease | 0.661 | 64.4 | 9.36 | 282 |
| Paget's disease | 0.813 | 34.3 | 5.31 | 116 |
| Paget's disease | 0.742 | 46.7 | 11.9 | 362 |
| Paget's disease | 0.822 | 32.9 | 7.5 | 306 |
| Paget's disease | 0.672 | 61.7 | 7.5 | 221 |
| Normal | 1.023 | 8.34 | 2.89 | not measured |
| Normal | 0.881 | 24.7 | 2.78 | not measured |

① Collagen peptide concentration [ng/ml]
② Collagen peptide concentration [ng/ml] referred to the creatinine concentration [µmol]
③ Bone collagen equivalents concentration [pmol] referred to the creatinine concentration [nmol]

Figure 3:
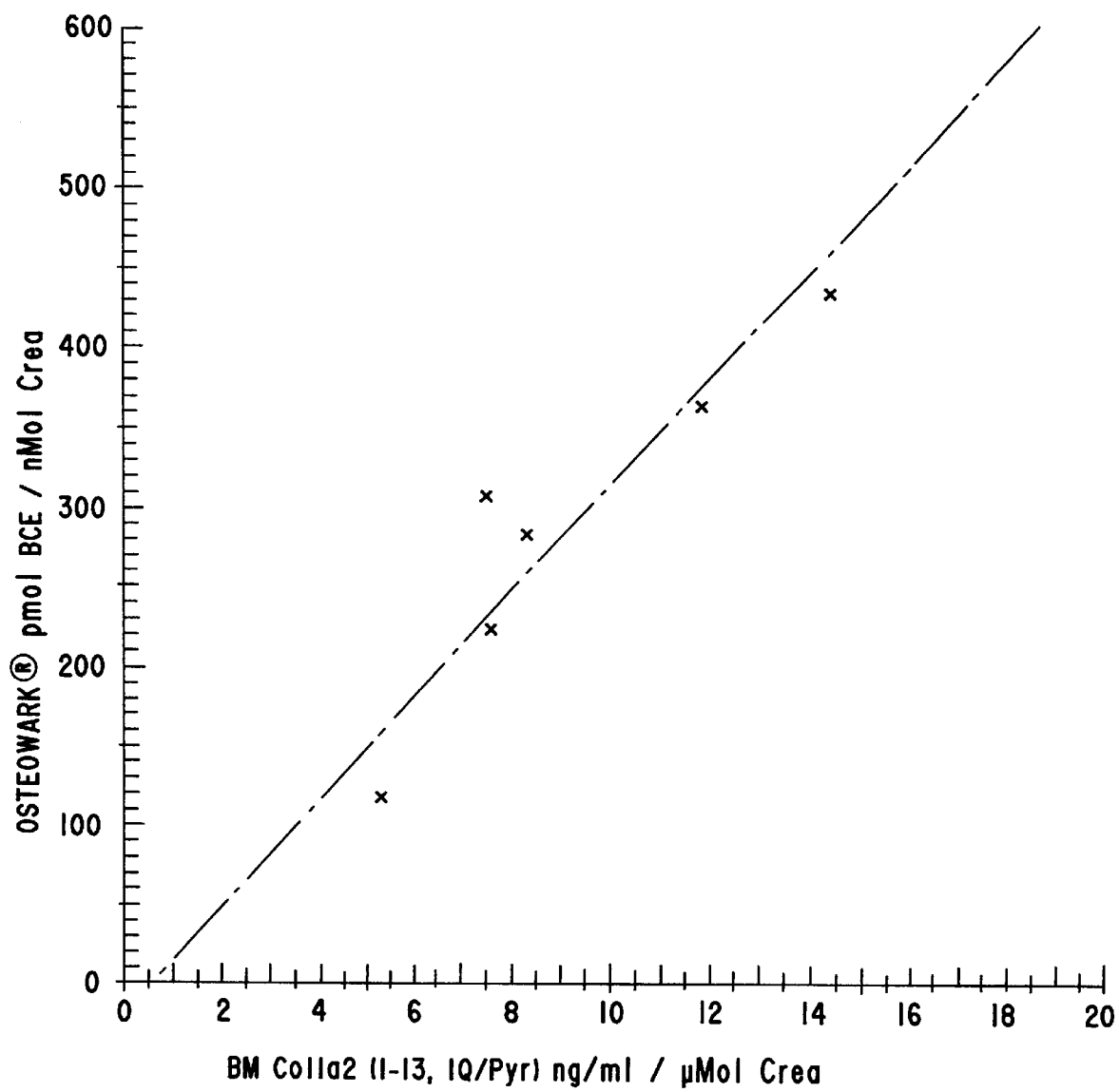
FIG. 3 shows a correlation between the tests of the invention and the OSTEOMARK® test.

FIG. 3 shows the correlation between the test of the invention and the OSTEOMARK® (an assay for the measurement of cross linked N-telopeptides of type 1 collagan in human urine) test. A coefficient of correlation of 0.925 was obtained.

Figure 4:
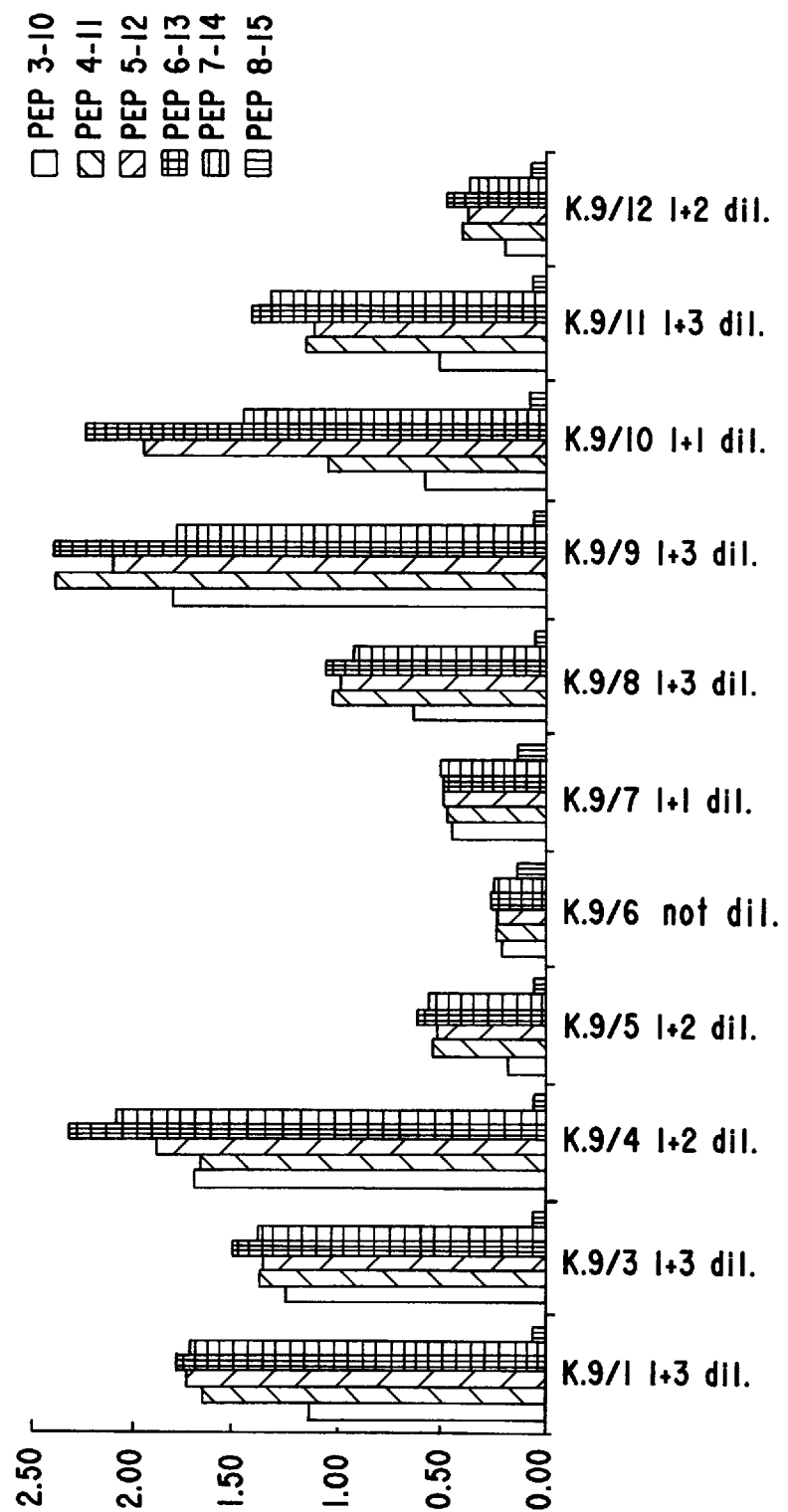
FIG. 4 and 5 show the results of a PEPSCAN® analysis carried out with culture supernatants of spleen cells of mice 328/11 and 328/14 that were fused with the myeloma cells.
Figure 5:
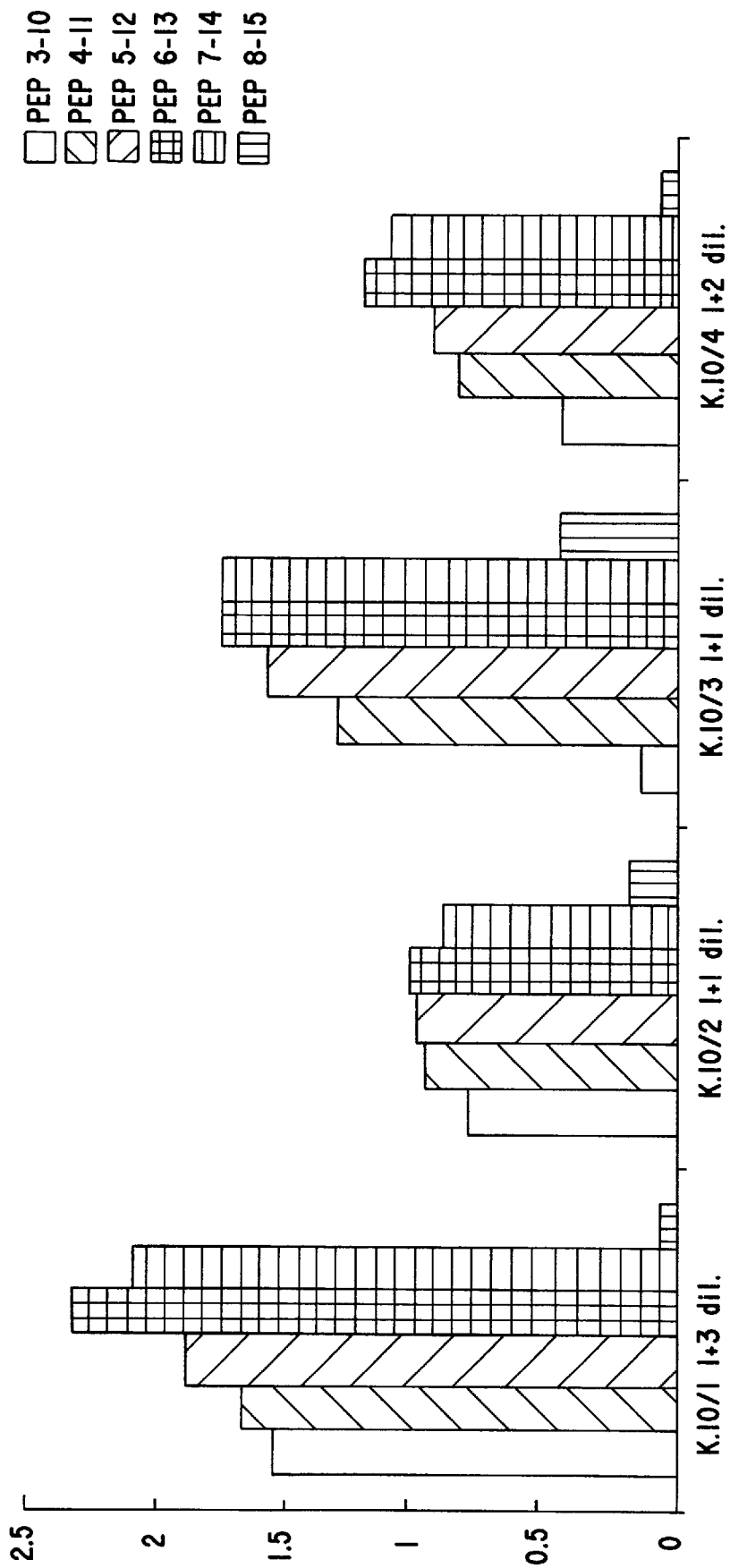

The spleen cells of the mice 328/11 and 328/14 that were fused with the myeloma cells were placed in a culture. A Pepscan analysis was carried out with the culture supernatants 9/1 to 9/12 (mouse 328/11) and 10/1 to 10/4 (mouse 328/14). The results are summarized in FIGS. 4 and 5.

The test procedure corresponds to example 3.1, however, with the following variants:

3.3 Pepscan measurements in primary cultures

Only the peptides Colllα2(3–10) to Colllα2(8–15) were used as biotin derivatized peptides. The mouse sera were replaced by culture supernatant 9-1 to 9-12 and 10-1 to 10-4 in varying dilution degrees (PBS, 0.05%, Tween 20).

The degree of dilution is given in the figure. Standard curves were obtained using the antibody-containing culture supernatant; the urine samples were measured and a correlation to the bone resorption marker OSTEOMARK® was determined. An example used for the procedure employed is an EIA competition test with the monoclonal antibodies of the culture supernatant 9-1 (mouse 328/11) (example 3.4).

3.4 EIA competition test with a monoclonal antibody

Figure 6:
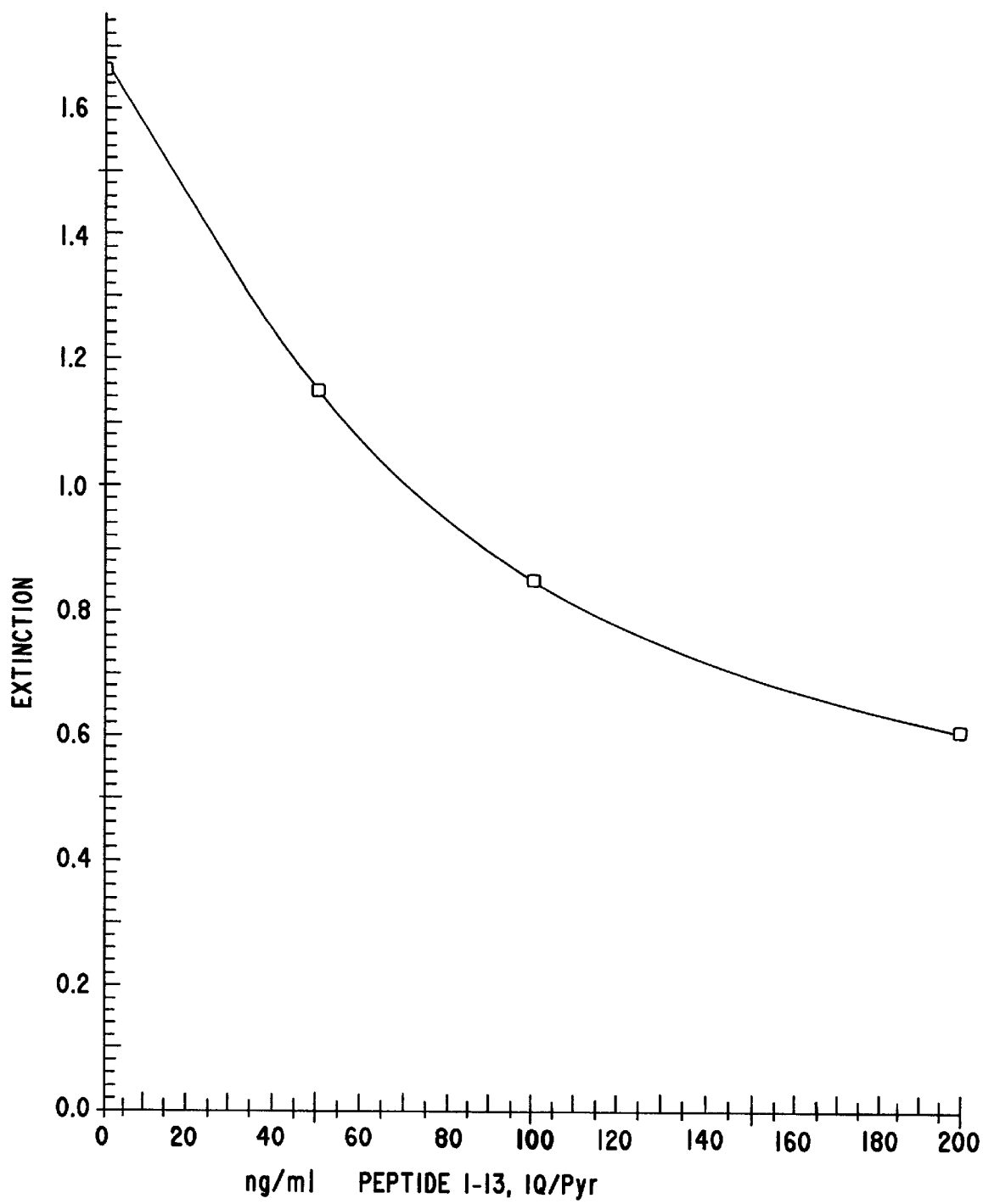
FIG. 6 shows a standard curve obtained using tissue culture supernatant and plotting the measuring signal generated with a POD-labeled Fab fragment of a polyclonal antibody to mouse Fcy, plotted against the standard concentration.

Thermo-BSA-streptavidin-coated microtiter plates were coated with biotinylated peptide Colllα2(6–13) (100 ng/ml PBS, 0.05% Tween 20, portions of 100 μl/well). After incubation for 1 hour at room temperature, the solution was washed twice with PBS, 0.05% Tween 20. The following concentrations were obtained from the peptide mixture Colllα2(1–13, 1 Gln/Pyr) by dilution with PBS, 0.05% Tween 20:0, 50,100, 200 ng/ml. 50 μl of the respective standard and 50 μl of the culture supernatant (1+1 diluted in PBS, 0.05% Tween 20) were pipetted into each well and mixed. After incubation for 1 h at room temperature, the solution was washed 3 times with PBS, 0.05% Tween 20; subsequently, as described for the Pepscan measurement, the measuring signal was generated with a POD-labeled Fab fragment of a polyclonal antibody to mouse Fcγ followed by a color reaction. The standard curve is obtained by plotting the measuring signal against the standard concentration, which is shown in FIG. 6.

Measuring the samples (urine)

Figure 7:
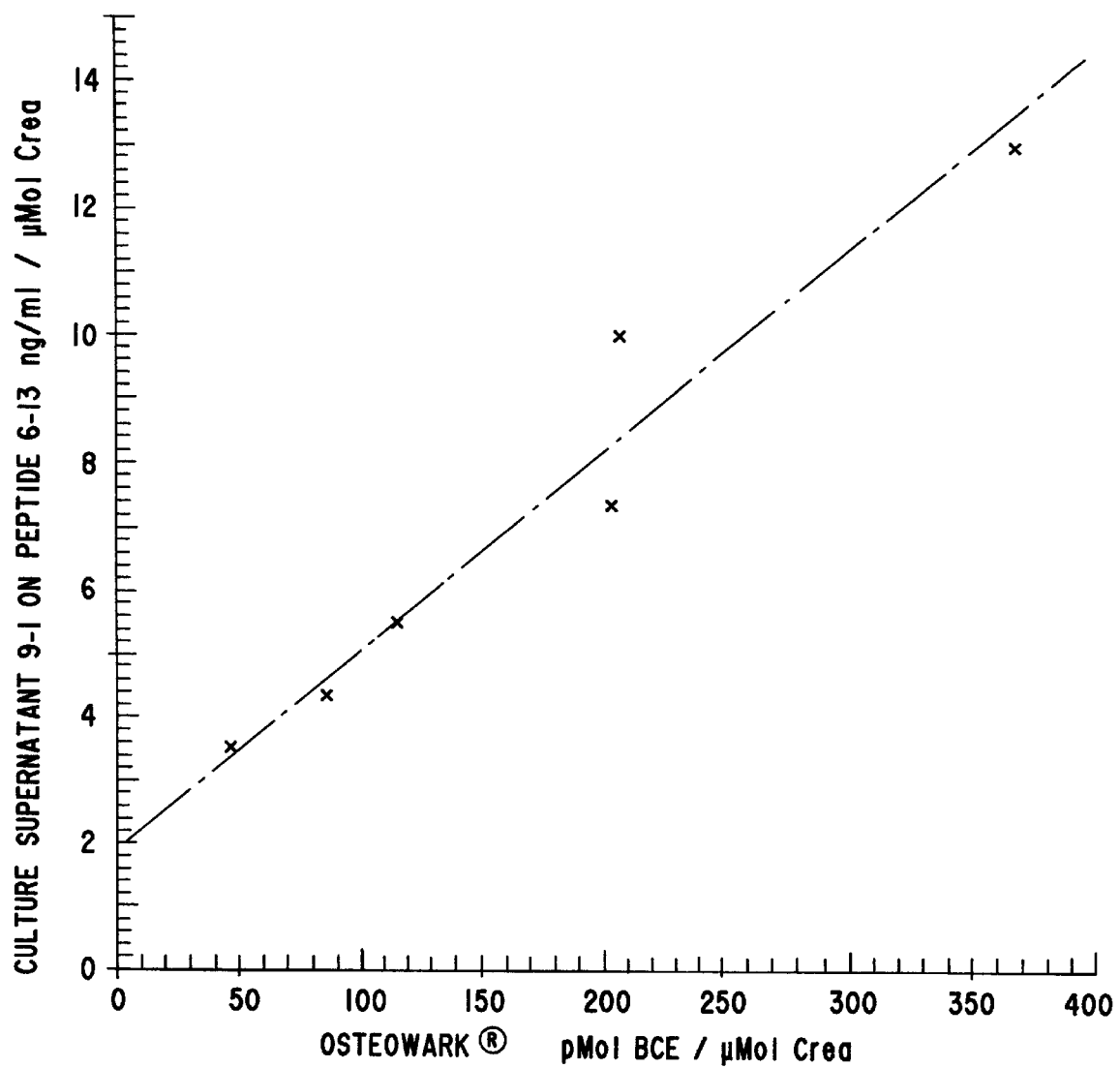
FIG. 7 shows a correlation between the OSTEOMARK® test and the test of the invention.

In the test, the standard dilutions were replaced by 50 μl of urine. The test procedure was otherwise carried out as were the standard curve. The concentration of the sample was read off the calibration curve and subsequently referred to the creatinine value of the sample. As regards the creatinine determination and the OSTEOMARK® test, the statements made in example 3.2 apply. The results are summarized in the following Table 2. The correlation to the OSTEOMARK® test is given in FIG. 7. A coefficient of correlation of 0.972 was obtained.

TABLE 2

| | | Test of the invention | | OSTEOMARK |
|---|---|---|---|---|
| Samples | Absorbance | Concentration ① | Concentration ② | Concentration ③ |
| Stand. | 1.663 | | | |
| Stand. 50 | 1.153 | | | |
| Stand. 100 | 0.852 | | | |
| Stand. 200 | 0.615 | | | |
| Normal urine | 1.103 | 56 | 4.34 | 86 |
| Normal urine | 1.181 | 47 | 3.48 | 48 |
| Paget's disease | 0.866 | 96 | 12.97 | 368 |
| Paget's disease | 1.044 | 64 | 7.36 | 204 |
| Paget's disease | 0.735 | 135 | 5.47 | 116 |
| Osteoporosis | 1.439 | 22 | 10 | 208 |

For ①, ② and ③: see Table 1

Table 3 summarizes data for additional culture supernatants. All cases showed a very good correlation to the OSTEOMARK® test.

TABLE 3

| Culture supernatant | Dilution | 0 hours mA | 200 ng/ml mA | Number of urine samples | Correlation to OSTEOMARK r |
|---|---|---|---|---|---|
| 9-1 | 1 + 1 | 1663 | 615 | 6 | 0.972 |
| 9-3 | 1 + 2 | 1391 | 397 | 5 | 0.995 |
| 9-4 | 1 + 2 | 1536 | 334 | 5 | 0.964 |
| 9-8 | 1 + 1 | 953 | 222 | 5 | 0.977 |
| 9-9 | 1 + 59 | 1349 | 341 | 8 | 0.925 |
| 10-2 | undiluted | 461 | 114 | 4 | 0.949 |

0 hours: lowest standard
200 ng/ml: highest standard
r: Coefficient of correlation

We claim:

1. A method for determining collagen degradation products in a body fluid sample which contains collagen degradation products using a non-competitive immunoassay, comprising:

incubating the body fluid sample with an antibody which specifically binds with the complete amino acid sequence of SEQ ID NO: 2 of collagen l; and determining the collagen degradation products bound to the antibody.

2. A method of claim 1, wherein the body fluid sample is denatured before the incubating step.

3. A method of claim 2, wherein the denatured body fluid sample is diluted before the incubating step.

4. A method for determining collagen degradation products in a body fluid sample which contains collagen degradation products using a competitive immunoassay, comprising:

incubating the body fluid sample with an antibody which specifically binds with the complete amino acid sequence of SEQ ID NO: 2 of collagen l, the body fluid sample and a peptide which competes with the collagen degradation products in the body fluid sample for binding to the antibody; and determining the collagen degradation products bound to the antibody.

5. A method of claim 4, wherein the body fluid sample and the peptide are incubated simultaneously.

6. A method of claim 4, wherein the body fluid sample and the peptide are incubated sequentially.

7. A method of claim 4, wherein the body fluid sample is denatured before the incubating step.

8. A method of claim 7, wherein the denatured body fluid sample is diluted before the incubating step.

9. A method of claim 4, wherein the immunoassay is selected from the group consisting of an enzyme immunoassay, a cloned enzyme donor immunoassay, a fluorescence polarization immunoassay, a turbidimetric inhibition immunoassay and a latex particle immunoassay.

10. A kit for determining collagen degradation products in a body fluid sample using a competitive immunoassay, comprising an antibody which specifically binds with the complete amino acid sequence of SEQ ID NO; 2 of collagen l and a peptide which competes with the collagen degradation products in the body fluid sample for binding to the antibody.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear -continued

```
    ( i i ) MOLECULE TYPE: peptide ( i x ) FEATURE:
            ( A ) NAME/KEY: misc_feature
            ( B ) LOCATION: 1
            ( D ) OTHER INFORMATION: /note= "Xaa at position 1 is Gln
                  or Pyr."

( x i ) SEQUENCE DESCRIPTION: SEQ ID NO:1:

Xaa  Tyr  Asp  Gly  Lys  Gly  Val  Gly  Leu  Gly  Pro  Gly  Pro  Cys
1                   5                        10

( 2 ) INFORMATION FOR SEQ ID NO:2:

( i ) SEQUENCE CHARACTERISTICS:
            ( A ) LENGTH: 4 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:2:

Val  Gly  Leu  Gly
1

( 2 ) INFORMATION FOR SEQ ID NO:3:

( i ) SEQUENCE CHARACTERISTICS:
            ( A ) LENGTH: 8 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:3:

Gly  Val  Gly  Leu  Gly  Pro  Gly  Pro
1                   5
```